United States Patent [19]
Kunze et al.

[11] Patent Number: 5,230,867
[45] Date of Patent: Jul. 27, 1993

[54] EXTENDED RELEASE FRAGRANCE DISPENSING CARTRIDGE

[75] Inventors: Walter A. Kunze, Southington; Robert J. Semanchik, Oxford, both of Conn.

[73] Assignee: Waterbury Companies, Inc., Waterbury, Conn.

[21] Appl. No.: 681,236

[22] Filed: Apr. 5, 1991

[51] Int. Cl.⁵ ............................................. A61L 9/12
[52] U.S. Cl. ..................................... 422/123; 422/5; 422/124; 422/306; 261/95; 261/101; 261/DIG. 17; 261/DIG. 65; 239/53; 239/55; 239/56; 239/57; 428/905
[58] Field of Search .................. 422/123, 124, 5, 306; 261/95, 101, DIG. 17, DIG. 65; 239/53, 55, 56, 57; 428/36.5, 905

[56] References Cited

U.S. PATENT DOCUMENTS

| | | | |
|---|---|---|---|
| D. 241,228 | 8/1976 | Boduch | D9/220 |
| D. 291,242 | 8/1987 | Harden et al. | D23/150 |
| D. 306,974 | 4/1990 | Tholstrup | D9/424 |
| D. 314,704 | 2/1991 | Lillelund et al. | D9/414 |
| D. 315,202 | 3/1991 | Kunze | D23/366 |
| 1,954,893 | 4/1934 | Saeks | 299/24 |
| 2,991,517 | 7/1961 | Bundy | 21/124 |
| 3,547,299 | 12/1970 | Kepple | 220/4 |
| 3,606,998 | 9/1971 | LaPorte et al. | 21/74 |
| 4,035,451 | 7/1977 | Tringali | 261/101 |
| 4,157,787 | 6/1979 | Schwartz | 239/56 |
| 4,356,969 | 11/1982 | Obermayer et al. | 239/6 |
| 4,383,951 | 5/1983 | Palson | 261/30 |
| 4,544,592 | 10/1985 | Spector | 239/56 |
| 4,580,581 | 4/1986 | Reece et al. | 131/231 |
| 4,634,614 | 1/1987 | Holzner | 239/55 |
| 4,753,389 | 6/1988 | Davis | 239/56 |
| 4,915,301 | 4/1990 | Munteanu | 239/55 |
| 5,019,434 | 5/1991 | Matsumoto | 239/55 |

FOREIGN PATENT DOCUMENTS 0003003  7/1979  European Pat. Off. .
1386465  3/1975  United Kingdom .

*Primary Examiner*—Lynn M. Kryza
*Attorney, Agent, or Firm*—Pennie & Edmonds

[57] ABSTRACT

A cartridge for an air freshener is disclosed, having a pad sealed within a housing by an air-permeable membrane. The density, permeability, and fiber characteristics of the pad and membrane are selected to achieve extended life while maintaining satisfactory air freshening performance.

30 Claims, 7 Drawing Sheets

EXTENDED RELEASE FRAGRANCE DISPENSING CARTRIDGE

FIELD OF THE INVENTION

The present invention relates to fragrance cartridges used to release a fragrance into the surrounding environs over an extended period of time.

BACKGROUND OF THE INVENTION

Air fresheners are a familiar product used both industrially and domestically to modify the olfactory properties of an enclosed atmosphere. Some of these fresheners are designed to remove undesired odors from the atmosphere, while others add desired odors.

Several types of fresheners have been developed in the latter category of odor-dispensing units. One type employs a can of a solid or liquid aromatic agent, placed in a housing mounted in the space to be freshened. Dispersal of the fragrance can be allowed to occur passively by movement of air within the space past the exposed agent. Alternatively, the housing may be equipped with a fan or similar means for promoting dispersal. Once the agent is exhausted, the can or other container is discarded and a refill can is emplaced.

These containers have significant drawbacks for certain markets. The agent itself can be a messy substance, especially in its liquid form. It therefore requires the exercise of considerable caution to avoid spillage or other mishaps. In addition, the aromatic agent in these dispensers evaporates quickly, so that large containers, and hence cumbersome housings, are required if the supply is to last for any significant period of time.

To meet the demand for a compact, easily handled product, fragrance cartridges were developed. The cartridges use pads treated with an odoriferous agent and mounted in a housing of convenient size. Like the aromatic agent containers, cartridges are made for a single usage, after which they are discarded.

One construction for these cartridges which is known in the art uses a pad treated with an aromatic agent and placed in a trough-like housing. The open top of the housing is sealed with a permeable material that allows dispersal of the fragrance.

Cartridge-type air fresheners have advantages over their more cumbersome counterparts described earlier, in terms of convenience, neatness and the like. However, known cartridge-type fresheners have until now been unreliable in terms of their ability to dispense a sufficiently strong aroma for a significant length of time. Generally, such cartridges are effective only for about 2 weeks or less. This is largely due to the fact that the fragrant agent is released too quickly through the permeable material. In designing cartridge dispensers, it has therefore become a primary concern to balance the properties of dispersal rate and cartridge life.

It is therefore an object of this invention to provide a convenient, cartridge-type air freshener that has a long life.

It is a further object of this invention to provide such an air freshener that releases an aroma at a rate adequate to conventional applications.

It is another object of the invention to provide a method of making such cartridges that yields products having predetermined, desired properties of life and release rate.

SUMMARY OF THE INVENTION

These and other objects that would be apparent to one skilled in the art are satisfied by the present invention, which comprises a polyester pad sealed within a housing by a polyester membrane. The properties of the pad and the membrane, including density, denier, and permeability, are selected to provide a desired fragrance release rate and cartridge life. Specifically, the pad has a density of between about 50 and 150 oz./yd.$^2$ and a denier of between about 1.5 and 9. The membrane has a denier of between about 4 and 4.5, a density of between about 1.5 and 9 oz./yd.$^2$ and an air permeability of between about 100 and 400 CFM/ft.$^2$ The combination of these components allows the cartridge to provide a preferred release rate of fragrance of about 0.55 to 0.9 grams per day. For optimum results, a release rate of 0.6 to 0.8 gram per day is utilized.

Preferred embodiments of the invention provide an effective fragrance release rate over a cartridge life of at least 20 and preferably about 28 to 30 days or longer, if desired. One of these embodiments employs a pad having a density of about 120-135, and most preferably 128 oz./yd.$^2$ and a denier of about 6, in combination with a membrane having a density of about 2.9 to 3 and most preferably 2.95 oz./yd.$^2$, a permeability of about 250 CFM/ft.$^2$, and a denier of about 4.4.

Another of these embodiments uses a pad having a density of about 65-80 and most preferably 72 oz./yd.$^2$ and a denier of about 3, and a membrane having a density of about 6 oz./yd.$^2$, a permeability of about 150 CFM/ft.$^2$ and a denier of about 4.4.

In a preferred construction, the housing includes an opening defined by a lip portion, a shoulder spaced from the lip portion for supporting and attaching the membrane thereto, and a recess having a perimeter defined by the shoulder. The membrane thus secures the pad member in the recess, and a seal may be attached to the lip portion to retain vapors of the fragrance agent in the cartridge.

BRIEF DESCRIPTION OF THE DRAWINGS

The structure and preferred embodiments of the invention can best be understood by reference to the accompanying drawings, in which.

DETAILED DESCRIPTION OF THE PREFERRED EMBODIMENTS

Figure 1:
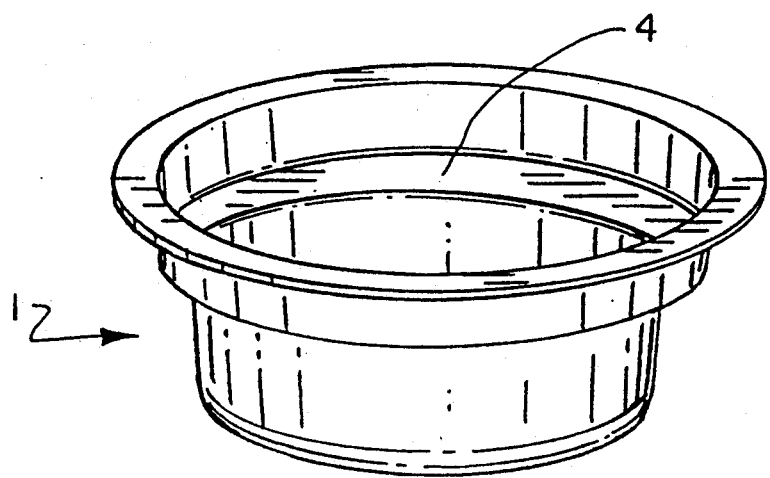
FIG. 1 is a perspective view of a circular air freshener cartridge according to the present invention.
Figure 2:
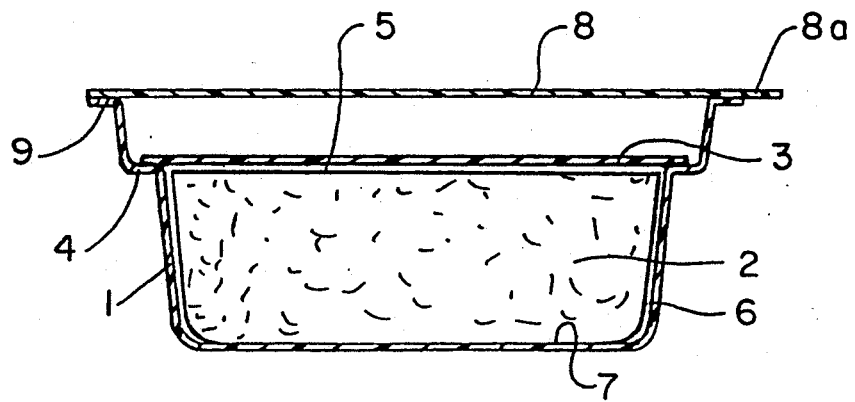
FIG. 2 is a cross sectional view of the air freshener of FIG. 1.

As shown by FIGS. 1 and 2, the structure of the air freshener cartridge of the present invention includes a housing 1 holding a pad 2 treated with an aromatic agent (not shown). The pad 2 is sealed within the housing 1 by a membrane 3, attached to the housing around a shoulder 4. Preferably, attachment of the membrane 3 to the shoulder 4 of the housing 1 is by an ultrasonic weld.

Both pad 2 and membrane 3 are preferably made of a polyester material. The specific material of the pad or membrane, however, is of lesser importance than its physical properties; in particular its density and air permeability properties.

Pad 2 is preferably ¾" thick and about 2" in diameter. Membrane 3 is usually between about 10 to 35 mils in thickness. The pad 2 should fit snugly within housing 1 so that evaporation of the aromatic agent occurs from the top surface 5 of the pad rather than from the sides 6 or bottom 7 of the pad. This ensures that the pad 2 acts as a wick, drawing the agent from the lower part of the pad to the top when the agent at the top is released to the environs.

A seal 8 is provided across the top of housing 1, joined to lip 9, for preventing release of the fragrance between the time of manufacture and the time of use. Seal 8 typically is made of foil, and is securely bonded to lip 9 by heat and pressure bonding. Alternatively, ultrasonic welding or a suitable adhesive may be used to make this bond. Seal 8 includes a tab 8a that can be gripped by the user to remove the seal when the fragrance is to be initially released from the cartridge.

Lip 9 allows seal 8 to be bonded thereto in a position away from pad 2, thereby affording a dry surface for providing a secure, airtight seal. In prior designs which do not include shoulder 9, it is difficult to achieve such a seal because pad 2 and membrane 3 become saturated with the aromatic agent, thus potentially causing a wet surface in the area where the seal 8 is to be bonded to the cartridge. Thus, after the cartridge was provided with the aromatic agent, it would be placed in a mylar package. In the present design, the membrane 3 is attached to the shoulder prior to introduction of the aromatic agent, and the seal 8 is later bonded to lip 9, thus eliminating the need for a mylar package.

The rate at which the aromatic agent is drawn to the top surface of the pad 2 will depend on the properties of the pad. If pad 2 is of high density and low porosity, then transmission of the agent to the surface of the pad will be slow. If pad 2 is of low density and high porosity, then the agent will be carried to the surface of the pad more rapidly.

The properties of the membrane 3 also affect the manner in which the fragrance agent is dispensed, by delimiting the rate of communication between the outside air and the fragrance agent at the surface of the pad. If the membrane has a high density and a low permeability, it will retard the dispensing of the fragrance to the atmosphere. If the membrane 3 has a low density and high permeability, then the fragrance will be released more rapidly.

Also, the specific type of fragrance agent and its physical properties contribute to the desired release rate. Generally, the active odor-producing ingredient is an organic oil-based perfume. Depending on cost and scent strength, it may be appropriate to mix the perfume with an odorless extender. A suitable extender for purposes of the present invention when aromatic organic oil-based perfumes are used, is Isopar, an odorless mineral oil.

According to the present invention, the properties of pad 2 are selected in combination with the properties of membrane 3 to achieve a desired, predetermined rate of fragrance release and cartridge life. Generally, a service life of at least about 20 days is easily achieved by the present invention. As mentioned earlier, prior art cartridges have employed light pads with light membranes, resulting in rapid depletion of the fragrance in the cartridge. The cartridges of the present invention provide a longer service life of satisfactory release rates for the fragrances. In particular, the life of the preferred cartridges of the present invention is about 28-30 days. Prior art devices, by contrast, provide a much lesser service life, which is on the order of one to two weeks with some lasting only 3-4 days. The present invention therefore constitutes an almost tenfold improvement over the prior art.

One particularly preferred embodiment of the present invention employs a pad 2 having a density of about 128 oz./yd.$^2$ and a denier of about 6 (denier is a characteristic of the fibers making up the material). This is considered a high density pad for purposes of the invention. Suitable materials for the pad of the present invention can be obtained from The Felters Company, located in Middlebury, Mass.

To counter the restrictive flow characteristics of the high density pad, a low density, high permeability membrane 3 is used. A suitable membrane material is REEMAY ® Style 2033, which has a density of about 2.95 oz./yd.$^2$, a permeability of about 250 CFM/ft.$^2$ and a denier of about 4.4.

Alternatively, a higher permeability membrane could be used, such as REEMAY ® Style 2295. Its density and denier are the same as the Style 2033, but the permeability is about 300 CFM/ft.$^2$ The combination of a flow-restrictive pad and flow-permissive membrane produces the balanced properties of long life and sufficient fragrance release.

If a longer fragrance release life were desired and a highly restricted rate of dispensation of the fragrance were acceptable, then a heavier density, lower porosity membrane could be used in combination with the high density pad. REEMAY ® Style 2470 is such a lower porosity material, having a density of about 6 oz./yd.$^2$, a permeability of about 150 CFM/ft.$^2$ and a denier of about 4.4.

The more preferable, balanced characteristics of the previous embodiments can alternatively be achieved in accordance with another preferred embodiment of the invention, which employs a low density pad 2 in combination with a high density, low permeability membrane 3. Thus, a pad 2 having a density of 72 oz./yd.$^2$ and a denier of about 3, which would dispense its store of aromatic agent relatively rapidly if exposed to open air, can be satisfactorily used. A suitable membrane for balancing the rapid dispensing characteristics of the pad is the REEMAY ® Style 2470. As stated above, this material has a density of about 6 oz./yd.$^2$, a permeability of 150 CFM/ft.$^2$ and a denier of about 4.4. This embodiment, like the embodiment using a high density pad with a low density membrane, can provide satisfactory performance for about 30 days.

Figure 3:
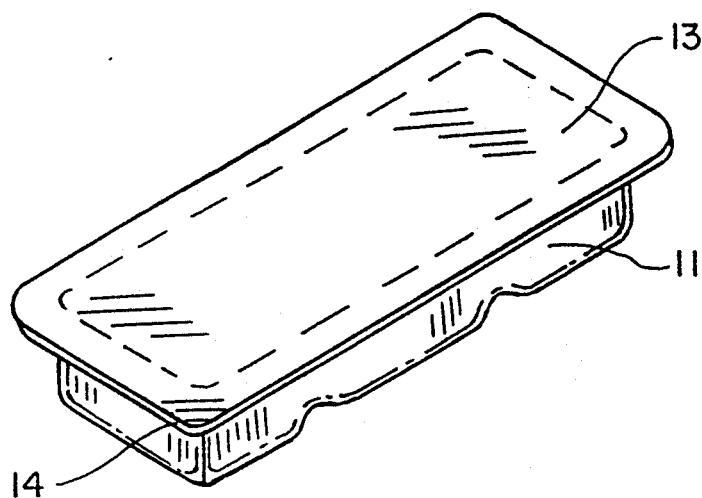
FIG. 3 is a perspective view of a rectangular air freshener cartridge according to the present invention.
Figure 4:
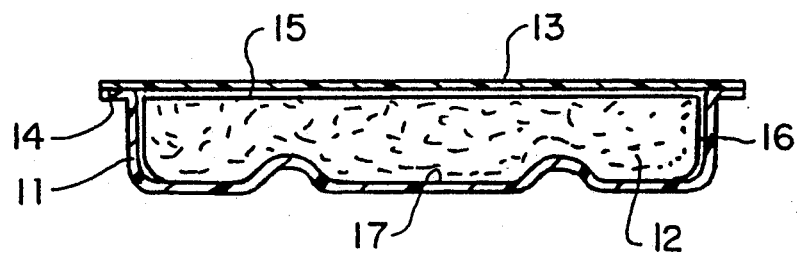
FIG. 4 is a cross-sectional view of the air freshener of FIG. 3.

FIGS. 3 and 4 show a rectangular embodiment of the present invention. Rectangular housing 11 holds a pad 12, and membrane 13 seals the pad in the housing around lip 14 of the housing. An aromatic agent (not shown) is released from the top surface 15 of the pad 12, and not the sides 16 or the bottom 17.

The rectangular embodiment shown in FIGS. 3 and 4 would be packaged in a sealed wrapper (not shown) to prevent fragrance release between the time of manufacture and the time of use. Alternatively, housing 11 could be provided with a shoulder and lip as in the circular embodiment of FIGS. 1 and 2, with the membrane joined across the shoulder and a seal across the lip.

Figure 5:
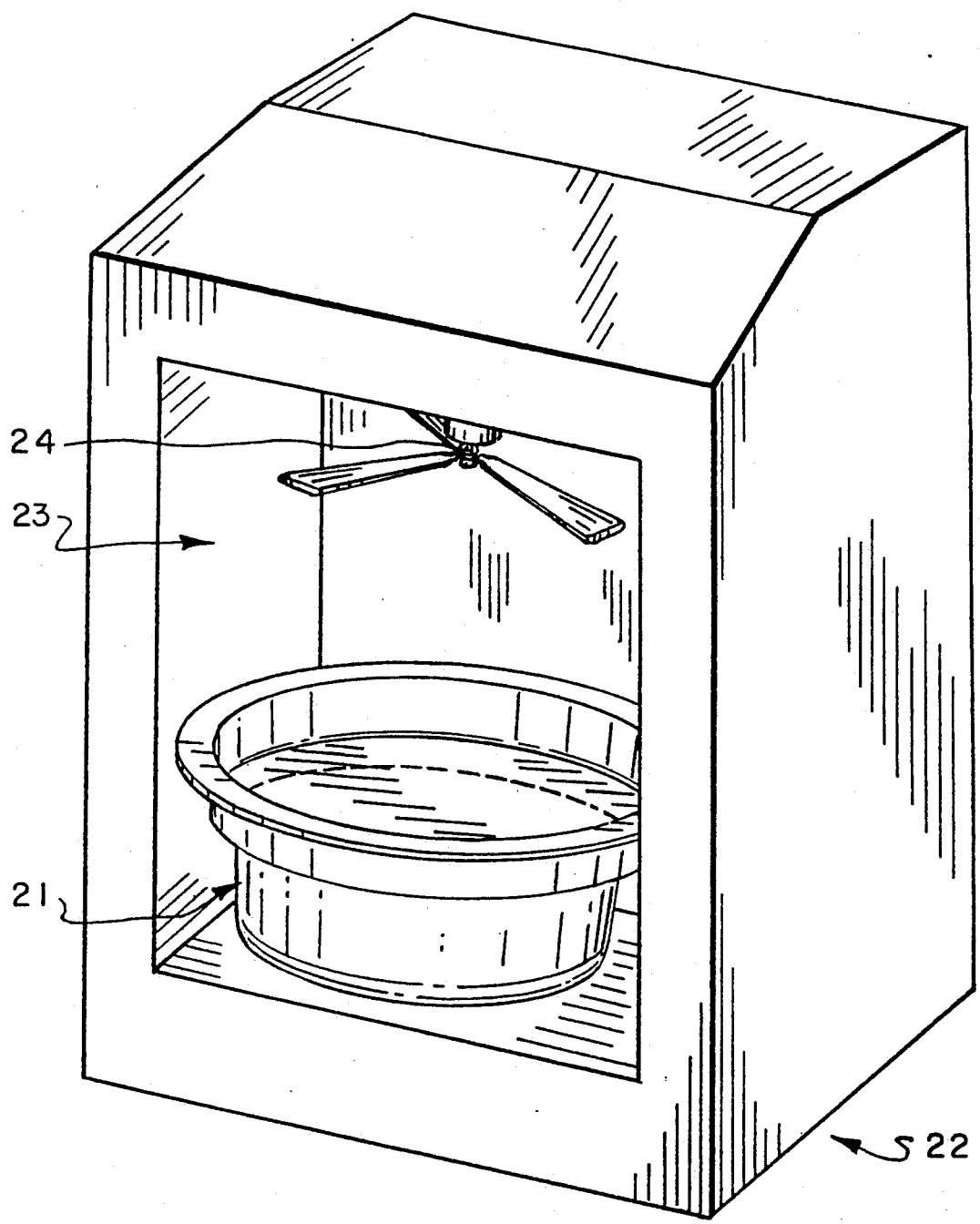
FIG. 5 is a perspective view of an air freshener dispenser used in conjunction with the air freshener cartridge of the present invention.

FIG. 5 illustrates a typical dispenser in which the cartridges 21 of the present invention might be used. The dispenser includes a cabinet 22, a compartment 23 for the cartridge 21, and a fan 24 to disperse the aromatic agent. The fan may be driven by a DC battery or AC current, as is known in the art.

To achieve the desired release rates, the effectiveness of certain combinations of pads and membranes are illustrated in FIGS. 6–9. Each embodiment used 1 ounce (28 grams) of an aromatic oil-based mint fragrance made by Carrubba Company, Milford, Conn. No extender was mixed with the fragrance agents in these embodiments.

Figure 6:
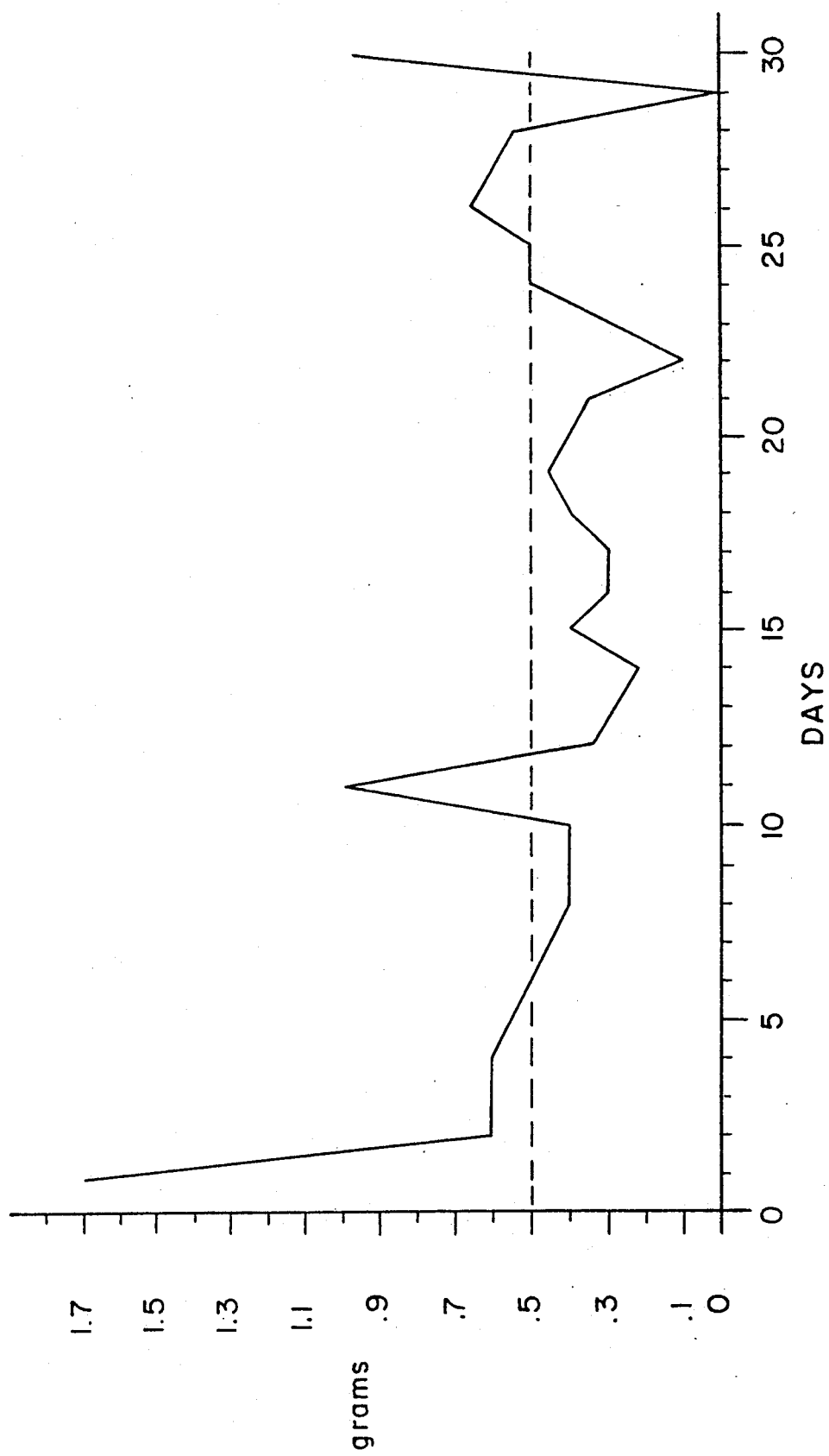
FIGS. 6-9 are graphs illustrating the release rate of the fragrance agent through different pad/membrane combinations.

FIG. 6 illustrates the combination of a hard (i.e. 6 denier and 128 oz./yd.$^2$) pad with the lower permeability membrane (i.e., 150 CFM/ft.$^2$ and 6 oz./yd.$^2$). A total release of 15 grams over a thirty day period for a release rate of 0.5 grams per day is achieved with this construction. This results in a low and relatively imperceptible release rate of fragrance agent into the surrounding environment. Such a construction is not preferred for most applications.

Figure 8:
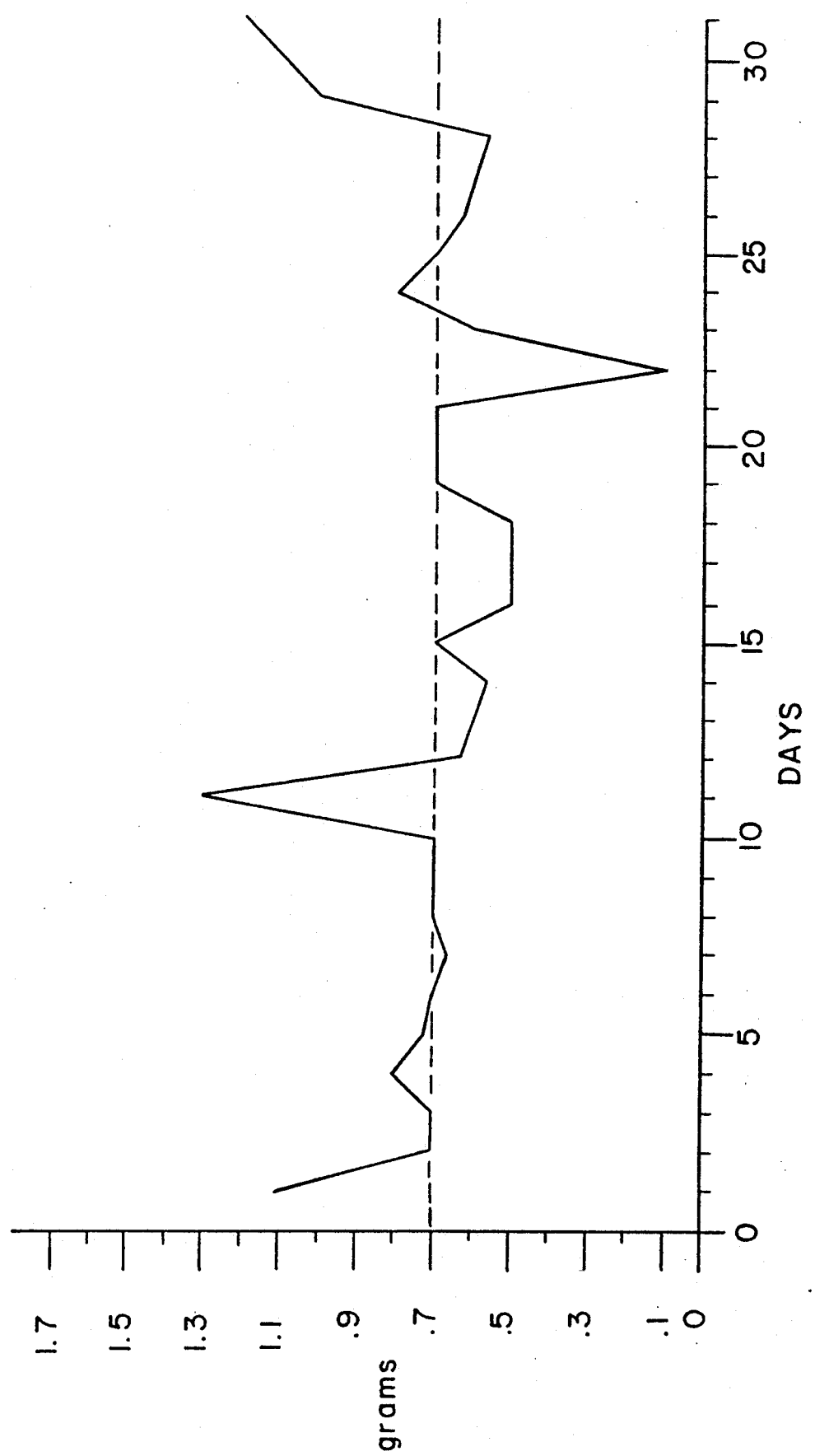

An improved release rate is obtainable with the pad of FIG. 6 and a higher permeability membrane (e.g., 250 CFM/ft.$^2$ and 2.95 oz./yd.$^2$). As shown in FIG. 8, a release of 21 grams (release rate 0.7 grams/day) is achieved, providing an entirely satisfactory fragrance agent distribution into the surrounding environment.

Figure 7:
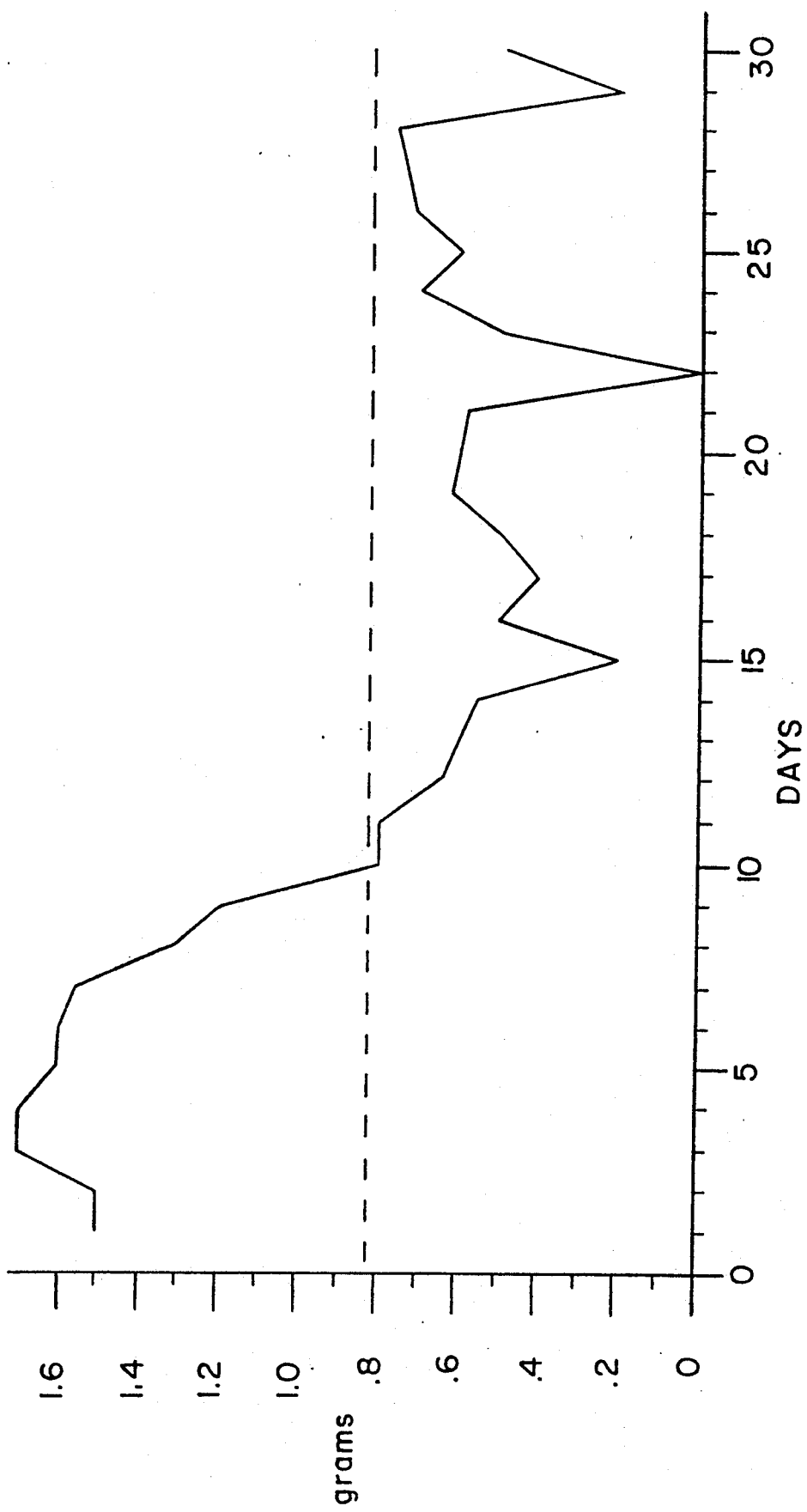

Similar good results are obtained with a combination of the lower permeability membrane (of FIG. 6) and the softer pad (FIG. 7). A release rate of about 0.8 grams/day (see FIG. 8) is achieved. As shown in FIG. 8, the fragrance agent is nearly depleted at the end of the 30 day test period. This combination can be considered to be near the desired upper limit, since a small amount of fragrance agent must remain at the end of the cycle to provide perceptible fragrance in the surrounding environment.

Figure 9:
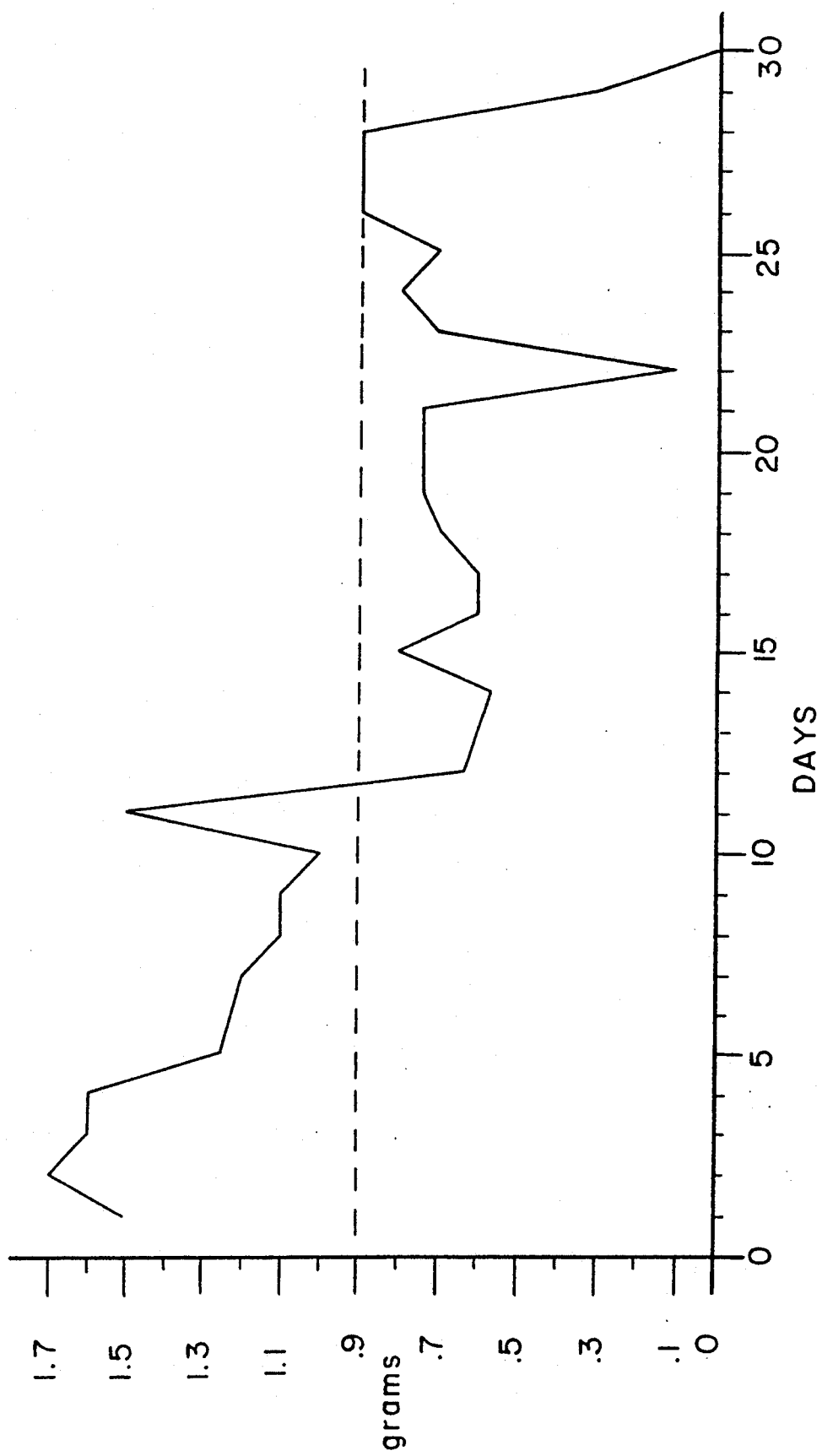

FIG. 9 illustrates another combination which, like that of FIG. 6, is not desired for most applications. The use of the higher permeability membrane (FIG. 7) with the softer pad (FIG. 6) provides a relatively high release rate of greater than 0.9 grams/day (a total release of the 28 grams over less than the entire 30 day cycle). The release rate is slightly too high, such that all fragrance is dispensed over less than the desired time.

From this data, it is possible for one skilled in the art to select appropriate combinations of pad and membrane materials, and fragrance agent, to achieve the desired release rate. These embodiments are intended to illustrate the invention and disclose its most preferred forms, but are not exhaustive of the scope of extended life fragrance cartridges taught by the present invention.

We claim:

1. An air freshening cartridge, comprising:
a housing having means defining an opening;
a pad member mounted in the housing, having an upper surface and having a density of between about 50 and about 150 oz./yd.$^2$;
a fragrance agent initially retained substantially within the pad member; and
a permeable membrane having a density of between about 1.5 oz./yd.$^2$ and 9 oz./yd.$^2$ and an air permeability of between about 100 CFM/ft.$^2$ and 400 CFM/ft.$^2$, said membrane covering the housing opening for retaining the pad member within the housing and positioned adjacent the pad member to allow the fragrance agent to be drawn through the pad member to the upper surface thereof to saturate the membrane, thus permitting the fragrance agent to communicate with an environment external to the housing opening through the membrane at a release rate of above about 0.55 to less than about 0.9 grams per day.

2. The cartridge of claim 1, wherein the density and denier of the pad member and the density, denier and permeability of the membrane are selected to provide an expected life for the fragrance agent of about 30 days at the stated release rate.

3. The cartridge of claim 1, wherein the pad has a density of between about 100 and 150 ox./yd.$^2$ 4. The cartridge of claim 3, wherein the membrane has a density of between about 2 oz./yd.$^2$ and 4 oz./yd.$^2$, and a permeability of between about 200 CFM/ft.$^2$ and 400 CFM/ft.$^2$, and the fragrance communicates with the environment at a release rate of between about 0.6 and 0.8 grams per day over a period of at least about 28 days.

5. The cartridge of claim 4, wherein the pad member has a denier of between about 5 and 9.

6. The cartridge of claim 5, wherein the membrane has a denier of between about 4 and 4.5.

7. The cartridge of claim 1, wherein the pad member has a density of between about 50 oz./yd.$^2$ and 100 oz./yd.$^2$ 8. The cartridge of claim 7, wherein the membrane has a density of between about 5 and 7 oz./yd.$^2$ and a permeability of between about 100 CFM/ft.$^2$ and 200 CFM/ft.$^2$ 9. The cartridge of claim 8, wherein the pad member has a denier of between about 1.5 and 5.

10. The cartridge of claim 9, wherein the membrane has a denier of between about 4 and 4.5.

11. The cartridge of claim 1 wherein the housing includes a recess for receiving the pad member and a shoulder for supporting and attaching the membrane, wherein the membrane retains the pad member in the recess.

12. The cartridge of claim 1 wherein the housing includes a lip portion defining the opening.

13. The cartridge of claim 12 wherein the housing further includes a seal attached to the lip portion to retain vapors of the fragrance agent in the cartridge.

14. An air freshening cartridge, comprising:
a housing having means defining an opening;
a pad member mounted in the housing, having an upper surface and having a density of between about 120 and about 135 oz./yd.$^2$;
a fragrance agent initially retained substantially within the pad member; and
a permeable membrane having a density of between about 1.5 oz./yd.$^2$ and 9 oz./yd.$^2$ and an air permeability of between about 100 CFM/ft.$^2$ and 400 CFM/ft.$^2$, said membrane covering the housing opening for retaining the pad member within the housing and positioned adjacent the pad member to allow the fragrance agent to be drawn through the pad member to the upper surface thereof to saturate the membrane, thus permitting the fragrance agent to communicate with an environment external to the housing opening through the membrane at a release rate of above about 0.55 to less than about 0.9 grams per day.

15. The cartridge of claim 14, wherein the membrane has a density of about 2.9 to 3oz./yd$^2$ and a permeability of between about 250 CFM/ft.$^2$ and 300 CFM/ft.$^2$.

16. The cartridge of claim 15, wherein the pad member has a denier of about 6.

17. The cartridge of claim 16, wherein the membrane has a denier of about 4.4.

18. The cartridge of claim 14, wherein the expected life for the fragrance agent is about least about 20 days at the stated release rate.

19. The cartridge of claim 18, wherein the expected life for the fragrance agent is at least about 28 days at the stated release rate.

20. The cartridge of claim 14 wherein the housing includes a recess for receiving the pad member and a shoulder for supporting and attaching the membrane, wherein the membrane retains the pad member in the recess.

21. The cartridge of claim 14 wherein the housing includes a lip portion defining the opening.

22. The cartridge of claim 21 wherein the housing further includes seal attached to the lip portion to retain vapors of the fragrance agent in the cartridge.

23. An air freshening cartridge, comprising:
   a housing having means defining an opening;
   a pad member mounted in the housing, having an upper surface and having a density of between about 65 and about 80 oz/yd.$^2$;
   a fragrance agent initially retained substantially within the pad member; and
   a permeable membrane having a density of between about 1.5 oz./yd.$^2$ and 9 oz./yd.$^2$ and an air permeability of between about 100 CFM/ft.$^2$ and 400 CFM/ft.$^2$, said membrane covering the housing opening for retaining the pad member within the housing and positioned adjacent the pad member to allow the fragrance agent to be drawn through the pad member to the upper surface thereof to saturate the membrane, thus permitting the fragrance agent to communicate with an environment external to the housing opening through the membrane at a release rate of above about 0.55 to less than about 0.9 grams per day.

24. The cartridge of claim 23, wherein the membrane has a density of about 6 oz./yd.$^2$ and a permeability of about 150 CFM/ft.$^2$ 25. The cartridge of claim 24, wherein the pad member has a denier of about 3.

26. The cartridge of claim 25, wherein the membrane has a denier of about 4.4, and the expected life for the fragrance agent is at least about 28 days at the stated release rate.

27. An air freshening cartridge, comprising:
   a housing having means defining an opening defined by a lip portion, a shoulder spaced from the lip portion and a recess having a perimeter defined by the shoulder;
   a pad member mounted in the housing recess, having an upper surface and having a density of between about 65 and about 80 oz./yd.$^2$;
   a fragrance agent initially retained substantially within the pad member; and
   a permeable membrane having a density of between about 1.5 oz./yd.$^2$ and 9 oz./yd.$^2$ and an air permeability of between about 100 CFM/ft.$^2$ and 400 CFM/ft.$^2$, said membrane covering the housing opening for retaining the pad member within the housing and positioned adjacent the pad member to allow the fragrance agent to be drawn through the pad member to the upper surface thereof to saturate the membrane, thus permitting the fragrance agent to communicate with an environment external to the housing opening through the membrane at a release rate of above about 0.55 to less than about 0.9 grams per day;
   wherein the shoulder support the membrane and is attached thereto, and the membrane retains the pad member in the recess.

28. The cartridge of claim 27 wherein the housing further includes a seal attached to the lip portion to retain vapors of the fragrance agent in the cartridge.

29. The cartridge of claim 28, wherein the density and denier of the pad member and the density, denier and permeability of the membrane are selected to provide an expected life for the fragrance agent of about 30 days at the stated release rate.

30. The cartridge of claim 29, wherein the membrane has a density of between about2 oz./yd.$^2$ and 4 oz./yd.$^2$, and a permeability of between about 200 CFM/ft.$^2$ and 400 CFM/ft.$^2$, and the fragrance communicates with the environment at a release rate of between about 0.6 and 0.8 grams per day over a period of at least about 28 days.

* * * * *